(12) United States Patent
Mistry et al.

(10) Patent No.: US 12,144,734 B2
(45) Date of Patent: *Nov. 19, 2024

(54) ROBOTIC BONE PREPARATION FOR INCREASING IMPLANT CONTACT SURFACE AREA

(71) Applicant: Mako Surgical Corp., Fort Lauderdale, FL (US)

(72) Inventors: Amit Mistry, Weston, FL (US); Gokce Yildirim, Weehawken, NJ (US)

(73) Assignee: Mako Surgical Corp., Weston, FL (US)

( * ) Notice: Subject to any disclaimer, the term of this patent is extended or adjusted under 35 U.S.C. 154(b) by 834 days.

This patent is subject to a terminal disclaimer.

(21) Appl. No.: 17/306,198

(22) Filed: May 3, 2021

(65) Prior Publication Data
US 2021/0251762 A1    Aug. 19, 2021

Related U.S. Application Data

(63) Continuation of application No. 16/003,420, filed on Jun. 8, 2018, now Pat. No. 11,026,796.
(Continued)

(51) Int. Cl.
*A61F 2/30* (2006.01)
*A61F 2/28* (2006.01)

(52) U.S. Cl.
CPC ............ *A61F 2/30771* (2013.01); *A61F 2/28* (2013.01); *A61F 2/2846* (2013.01); *A61F 2/30749* (2013.01); *A61F 2/30942* (2013.01); *A61F 2002/2835* (2013.01); *A61F 2002/2839* (2013.01); *A61F 2002/285* (2013.01); *A61F 2002/30011* (2013.01); *A61F 2002/3006* (2013.01); *A61F 2002/30108* (2013.01); *A61F 2002/30115* (2013.01); *A61F 2002/30136* (2013.01); *A61F 2002/30233* (2013.01); *A61F 2002/30235* (2013.01);
(Continued)

(58) Field of Classification Search
CPC .................................................. A61F 2/30767
See application file for complete search history.

(56) References Cited

U.S. PATENT DOCUMENTS

| | | | |
|---|---|---|---|
| 4,822,362 | A | 4/1989 | Walker et al. |
| 4,846,839 | A | 7/1989 | Noiles |

(Continued)

OTHER PUBLICATIONS

Extended European Search Report for Application No. EP18176658.5 dated Nov. 7, 2018.

*Primary Examiner* — Brian A Dukert
(74) *Attorney, Agent, or Firm* — Lerner David LLP

(57) ABSTRACT

A bone implant includes at least one bone-engaging surface designed to mate with an implant-engaging surface of a bone. In the preferred embodiment, the bone-engaging surface of the implant includes a wave pattern comprising at least one peak extending in a proximal direction or at least one valley extending in a distal direction. The implant-engaging surface of the bone also includes a matching wave pattern having at least one peak and valley. Upon mating the engaging surfaces, a bone-implant interface may be created wherein the peaks and valleys of the wave patterns are aligned. As a result, there is good surface contact area at the bone-implant interface which helps prevent loosening or rotating of the implant.

20 Claims, 10 Drawing Sheets

Related U.S. Application Data

(60) Provisional application No. 62/516,910, filed on Jun. 8, 2017.

(52) U.S. Cl.
CPC ............... *A61F 2002/30327* (2013.01); *A61F 2002/30329* (2013.01); *A61F 2002/30357* (2013.01); *A61F 2002/30604* (2013.01); *A61F 2/30767* (2013.01); *A61F 2002/30772* (2013.01); *A61F 2002/3092* (2013.01); *A61F 2002/3093* (2013.01); *A61F 2002/3096* (2013.01)

(56) References Cited

U.S. PATENT DOCUMENTS

| | | |
|---|---|---|
| 5,108,437 A | 4/1992 | Kenna |
| 5,658,349 A | 8/1997 | Brooks et al. |
| 5,702,449 A | 12/1997 | McKay |
| 5,725,592 A | 3/1998 | White et al. |
| 5,755,803 A | 5/1998 | Haines et al. |
| 6,165,221 A | 12/2000 | Schmotzer |
| 6,299,648 B1 | 10/2001 | Doubler et al. |
| 6,364,910 B1 | 4/2002 | Shultz et al. |
| 6,402,785 B1 | 6/2002 | Zdeblick et al. |
| 6,887,276 B2 | 5/2005 | Gerbec et al. |
| 7,025,790 B2 | 4/2006 | Parks et al. |
| 7,044,976 B2 | 5/2006 | Meswania |
| 7,520,901 B2 | 4/2009 | Engh et al. |
| 7,909,881 B2 | 3/2011 | Boucher et al. |
| 8,002,777 B2 | 8/2011 | Fox et al. |
| 8,444,699 B2 | 5/2013 | Metzger et al. |
| 8,721,722 B2 | 5/2014 | Shah et al. |
| 9,289,299 B2 | 3/2016 | Metzger et al. |
| 9,381,085 B2 | 7/2016 | Axelson, Jr. et al. |
| 9,427,334 B2 * | 8/2016 | Axelson, Jr. ....... A61B 17/1604 |
| 9,433,480 B2 | 9/2016 | Pelote |
| 2008/0039950 A1 | 2/2008 | Splieth et al. |
| 2010/0094429 A1 | 4/2010 | Otto |
| 2012/0041564 A1 | 2/2012 | Landon |
| 2012/0209391 A1 | 8/2012 | Cipolletti et al. |
| 2016/0045323 A1 | 2/2016 | Kovacs et al. |
| 2016/0151164 A1 | 6/2016 | Taylor et al. |
| 2017/0304059 A1 | 10/2017 | Hanson |

\* cited by examiner

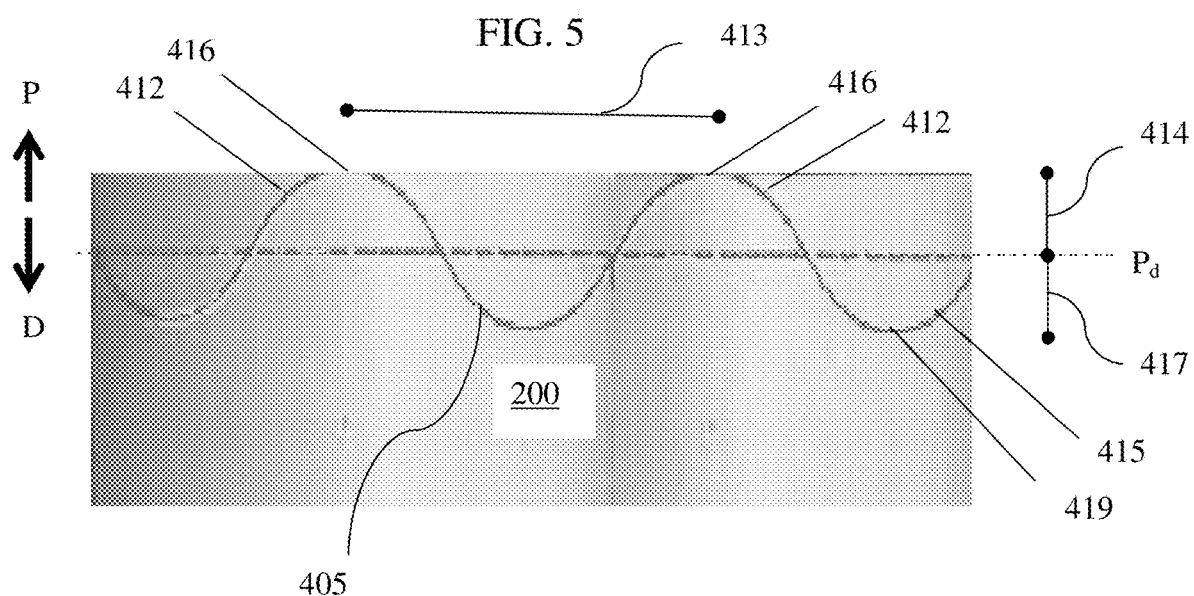

ROBOTIC BONE PREPARATION FOR INCREASING IMPLANT CONTACT SURFACE AREA

CROSS REFERENCE TO RELATED APPLICATION

The present application is a continuation of U.S. patent application Ser. No. 16/003,420, filed on Jun. 8, 2018, which claims the benefit of the filing date of U.S. Provisional Patent Application No. 62/516,910 filed Jun. 8, 2017, the disclosures of which are hereby incorporated herein by reference.

TECHNICAL FIELD

The present disclosure generally relates to orthopedic surgeries involving bone implants and methods of bone implant fixation. Disclosed herein are bone implants including a wave pattern on one or more of its bone-engaging surfaces and methods to maximize surface contact between a bone implant and a bone.

BACKGROUND OF THE INVENTION

Bone implants are often used to correct bone deformities resulting from trauma or degenerative conditions. For example, surgeons may position a bone implant between proximal and distal bone fragments in order to properly align the bone fragments in cases involving fractures, osteotomies, or other deformity conditions. Thus, the surgeon will mate at least one bone-engaging surface of the implant with an implant-engaging surface of the bone, thereby forming at least one bone-implant interface.

In many applications, a standard bone implant comes pre-manufactured and includes a planar bone-engaging surface. Intraoperatively, a surgeon may manually perform a bone cut, such as a straight planar bone cut, before positioning the bone implant. Then, the implant-engaging surface of the bone will match the bone-engaging surface of the implant and create a straight planar bone-implant interface.

Unfortunately, manual cutting can lead to imprecise bone cuts and chatter from cutting tools may further contribute to poor cutting precision. As a result, the implant-engaging surface of the bone may not be truly planar. Thus, there may be poor matching between the implant-engaging surface of the bone and the bone-engaging surface of the implant. For example, there may be gaps at the bone-implant interface. Over time, this can cause loosening or rotating of the bone implant, ultimately resulting in failure of implantation.

In some cases, a surgeon may choose to create a bore in the implant-engaging surface of the bone. Then, a keel or peg on the bone-engaging surface of the implant may be threaded or press fit into the bore in order to improve implant fixation. Still, poor matching at the bone-implant interface can lead to loosening or rotating of the bone implant and failure of implantation. Therefore, there is a need for bone implants that provide for better matching at the bone-implant interface and resist loosening or rotating of the bone implant.

SUMMARY OF THE INVENTION

A first aspect of the present disclosure is a bone implant comprising a proximal surface; and a distal surface having a wave pattern with at least one peak and at least one valley, wherein the distal surface is adapted to engage with an outer surface of a bone, and wherein the at least one peak extends towards the proximal surface in a proximal direction and the at least one valley extends away from the proximal surface in a distal direction. The distal surface may be porous. The distal surface may include a stem portion extending in the distal direction, the stem may a smaller diameter than a diameter of the distal surface. The stem may be insertable into a medullary canal of the bone, and may have proximal and distal ends. The distal end may be curved. The proximal surface may also include a head portion adapted to engage with a modular implant component. The head portion may also include a male connector.

The wave pattern on the distal surface of the implant can match a wave pattern on the outer surface of the bone, such that when the implant is operatively coupled to the bone the peaks and valleys of the respective implant and bone wave patterns are aligned. The implant may also include a cylindrical outer surface extending between the proximal and distal surfaces, wherein the proximal and distal surfaces are circular. The wave pattern may span only a circumferential perimeter of the distal surface. The wave pattern may have a periodic waveform. The peaks and/or valleys may have equal amplitude. The wave pattern may also have a uniform wavelength. The wave pattern may run along a single plane perpendicular to a central longitudinal axis of the bone. The wave pattern may also run along a plurality of planes at different angles with respect to a central longitudinal axis of the bone.

The proximal surface of the implant can include another wave pattern having peaks and valleys, the peaks extending away from the distal surface in a proximal direction and the valleys extending towards the distal surface in a distal direction. The wave patterns on the proximal and distal surfaces may match such that the peaks and valleys of the wave patterns are aligned.

The peaks and valleys may be preoperatively planned such that peaks align with relatively high density bone areas and valleys align with relatively low density bone areas. The proximal and distal surfaces may include an aperture extending therethrough, the aperture defining an inner surface. The implant may also include an outer surface extending between the proximal and distal surfaces, wherein the inner surface has a smaller diameter than a diameter of the outer surface.

The inner and outer surfaces may also include at least one fixation hole extending therethrough, the fixation hole adapted to receive a fixation element. At least one fixation hole may be adapted to receive the fixation element at a plurality of angles with respect to a central longitudinal axis of the bone. The inner and outer surfaces may also include a plurality of fixation holes of different sizes extending therethrough. At least one peak of the wave pattern on the proximal surface may align with at least one valley of the wave pattern on the distal surface. The proximal and distal surfaces may be parallel to one another. The proximal and distal surfaces may also be angled away from one another.

A second aspect of the present disclosure is a method of maximizing surface contact between an implant and an outer surface of a bone selecting a desired wave pattern for the outer surface of the bone, the wave pattern having at least one peak and at least one valley, the at least one peak extending in a proximal direction and the at least one valley extending in a distal direction; using a cutting tool to produce the wave pattern on the outer surface of the bone; and positioning the bone implant such that a distal surface of the bone implant engages the outer surface of the bone.

The positioning step may include disposing an adhesive on either the outer surface of the bone, the distal surface of the bone implant, or both. The method may also include producing a wave pattern on the distal surface of the bone implant. The wave patterns of the implant and the outer surface of the bone can match each other such that the peaks and valleys of the wave patterns are aligned. The method may also include determining the relative densities of areas of the bone, wherein the wave pattern of the bone is preoperatively planned such that peaks align with relatively high density bone areas and valleys align with relatively low density bone areas.

A third aspect of the present disclosure is another method of maximizing surface contact between an implant and an outer surface of a bone including selecting a desired wave pattern for a distal surface of the implant, wherein the wave pattern includes at least one peak and at least one valley, the at least one peak extending in a proximal direction and the at least one valley extending in a distal direction; producing the wave pattern on the distal surface of the implant; and positioning the implant such that the distal surface of the implant engages the outer surface of the bone.

The positioning step may include disposing an adhesive on either the outer surface of the bone, the distal surface of the bone implant, or both. The method may also include using a cutting tool to produce another wave pattern on the outer surface of the bone and the resulting wave patterns can match each other such that the peaks and valleys of the wave patterns are aligned. The method may include the step of determining the relative densities of areas of the bone wherein the wave pattern on the distal surface of the bone implant is preoperatively planned such that peaks align with relatively high density bone areas and valleys align with relatively low density bone areas.

The method may also include producing yet another wave pattern on a proximal surface of the bone implant and the resulting wave patterns on the proximal and distal surfaces can match each other such that the peaks and valleys of the wave patterns are aligned. At least one peak of the wave pattern on the proximal surface may be aligned with at least one valley of the wave pattern on the distal surface.

The method may additionally include engaging a proximal surface of the bone implant with a modular implant component. The method may further include inserting a fixation element through an aperture in an outer surface of the bone implant, the outer surface extending between the proximal and distal surfaces.

DESCRIPTION OF THE DRAWINGS

FIG. 5 shows a side view of the bone-implant interface of FIG. 4A.

DETAILED DESCRIPTION OF THE INVENTION

Those of skill in the art can recognize that the following description is merely illustrative of the principles of the disclosure, which may be applied in various ways to provide many different alternative embodiments.

Figure 1A:
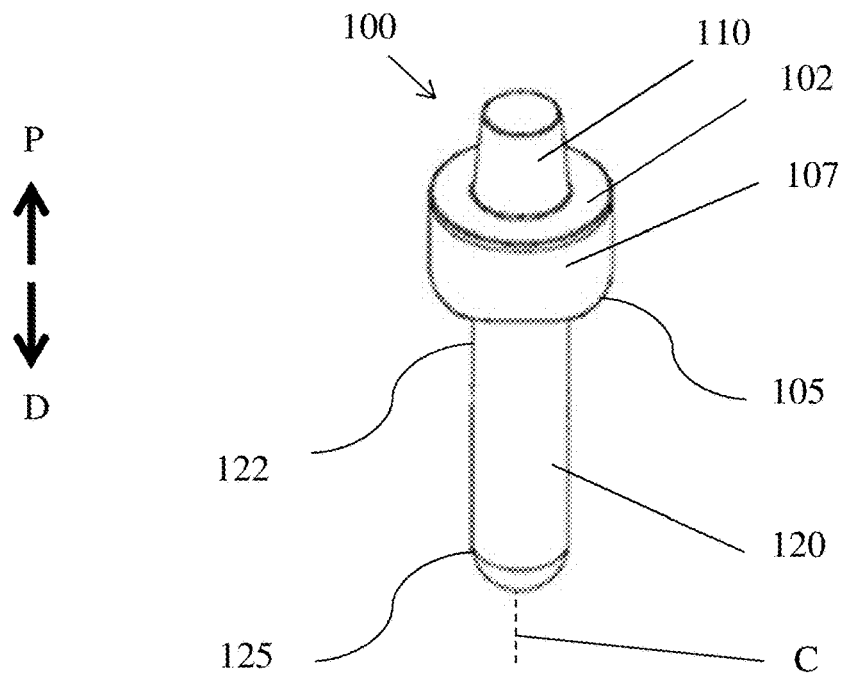
FIG. 1A shows a perspective view of a first embodiment of an implant of the present disclosure.
Figure 1B:
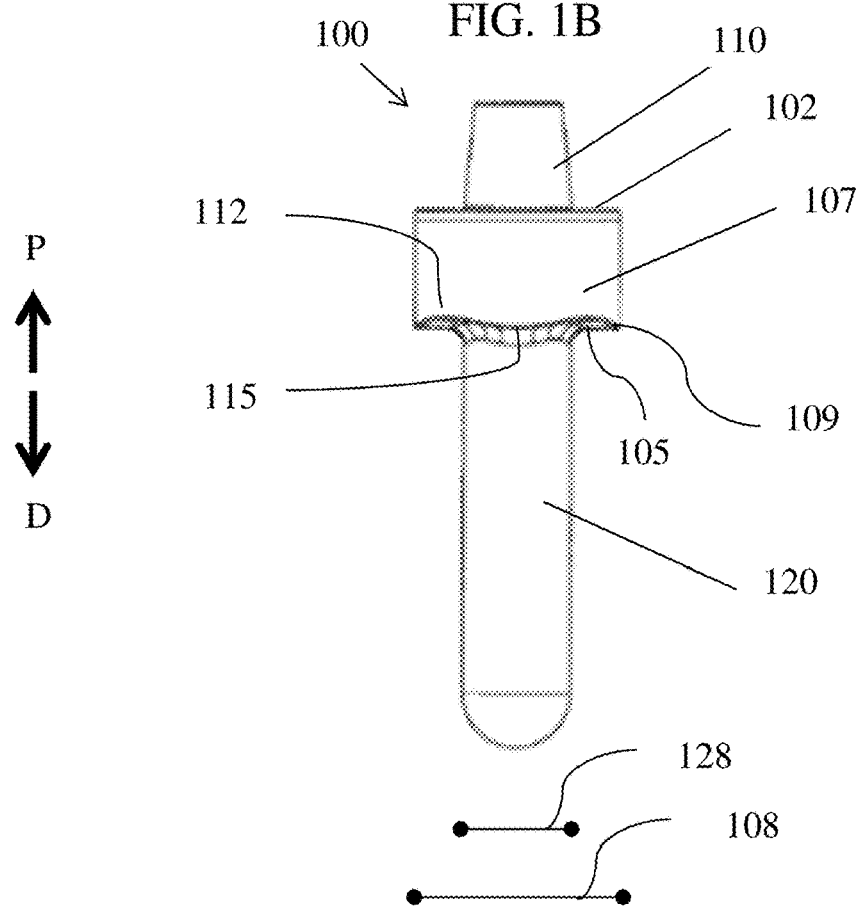
FIG. 1B shows a side view of the implant of FIG. 1A.
Figure 1C:
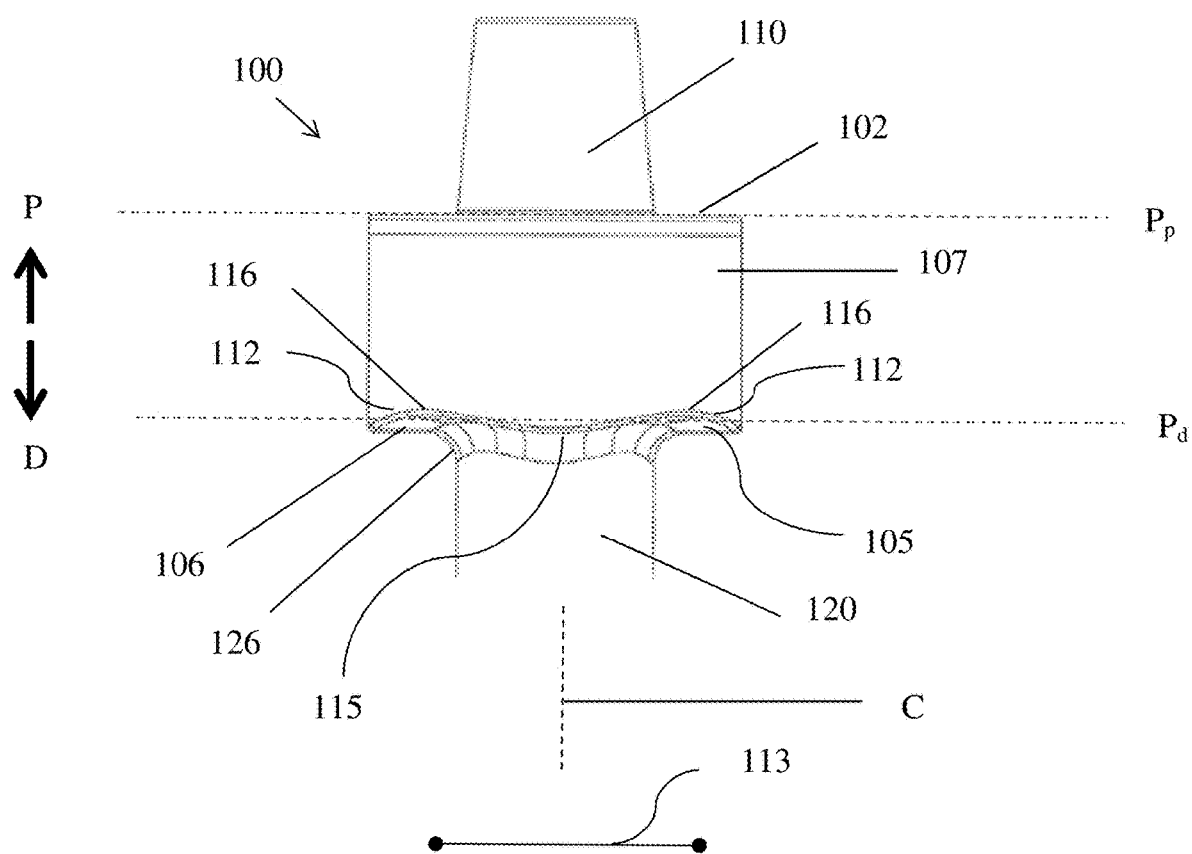
FIG. 1C shows a partial side view of the implant of FIG. 1A.

FIGS. 1A-1C show a bone implant 100 according to a first embodiment of the present disclosure. Implant 100 includes a circular proximal surface 102, a circular distal surface 105, and a cylindrical outer surface 107 extending between surfaces 102, 105. As shown, distal surfaces 105 is parallel to proximal surface 102 wherein distal surface 105 runs along axis Pa and proximal surface 102 runs along another axis Pp. Axes Pa and Pp are both perpendicular to a central longitudinal axis C.

Distal surface 105 is a bone-engaging surface and may be porous to allow for bone in-growth, resulting in improved implant fixation. This can be particularly useful for some embodiments where the distal surface is straight and planar. However, in the preferred embodiment, distal surface 105 includes a wave pattern having alternative peaks 112 and valleys 115 spanning its circumferential perimeter 109. The wave pattern is periodic meaning it repeats in regular intervals or periods. The wave pattern also has a uniform wavelength 113 which may be defined as a distance between adjacent centers 116 of peaks 112.

As shown, peaks 112 extend towards proximal surface 102 in a proximal direction P and valleys 115 extend away from proximal surface 102 in a distal direction D. Peaks 112 and valleys 115 may serve as rotational stabilizing features to improve implant fixation. That is, peaks 112 and valleys 115 may help maximize surface contact between distal surface 105 and an implant-engaging surface of the bone, as will be discussed further below. In many applications, additive manufacturing can be used to manufacture porous or solid peaks 112 and valleys 115 on the distal surface 105 of implant 100.

Distal surface 105 of implant 100 may also include a stem or keel portion, for example, cylindrical stem portion 120 extending in the distal direction D. As shown in FIGS. 1A-1C, stem portion 120 has proximal and distal ends 122, 125 and a diameter 128. Diameter 128 may be smaller than a diameter 108 of the distal surface 105. Both distal surface 105 and stem portion 120 may further include some adhesive 106, 126 respectively to help improve implant fixation.

Moreover, proximal surface 102 of implant 100 may include a head portion 110 which may engage with another modular implant component in certain applications, such as a hip implant system. Here, head portion 110 is a male connector.

Figure 2:
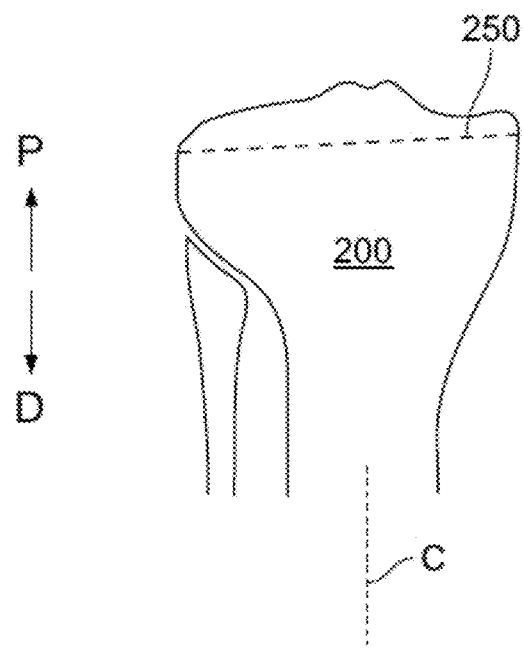
FIG. 2 shows a side view of a bone prior to planar bone cut being made.
Figure 3:
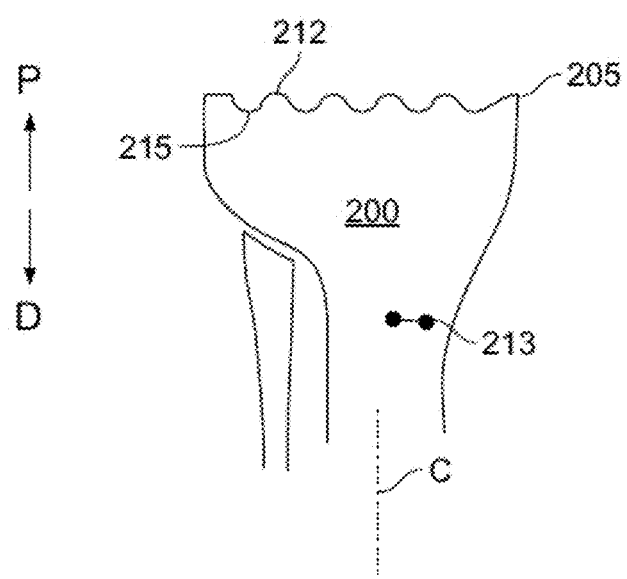
FIG. 3 shows a side view of the bone of FIG. 2 after a planar bone cut is made.

FIG. 2 shows a bone 200 extending along the central longitudinal axis C. FIG. 2 also shows an outline of a straight planar bone cut 250 that may be desired in certain applications. Accordingly, FIG. 3 shows bone 200 after the straight planar bone cut 250 has been made, thereby exposing an outer surface 205 of bone 200. Outer surface 205 of bone 200 is an implant-engaging surface.

A surgeon may further shape the outer surface 205 of bone 200 using a robotic cutting tool (not shown). For example, a surgeon may use the robotic cutting tool comprising a burr or similar surface finish tool to generate a wave pattern on the outer surface 205 of bone 200. The wave pattern may have alternating peaks 212 and valleys 215 corresponding to the peaks 112 and valleys 115 on implant 100, as will be discussed further below. As shown in FIG. 3, peaks 212 extend in the proximal direction P and valleys 215 extend in the distal direction D. Ultimately, including a wave pattern on both distal surface 105 and outer surface 205 can help maximize the contact area between surfaces 105, 205. Additionally, using a robotic cutting tool provides good precision to make accurate bone cuts. In turn, this may help reduce the amount of time required to prepare the bone before implantation.

Figure 4A:
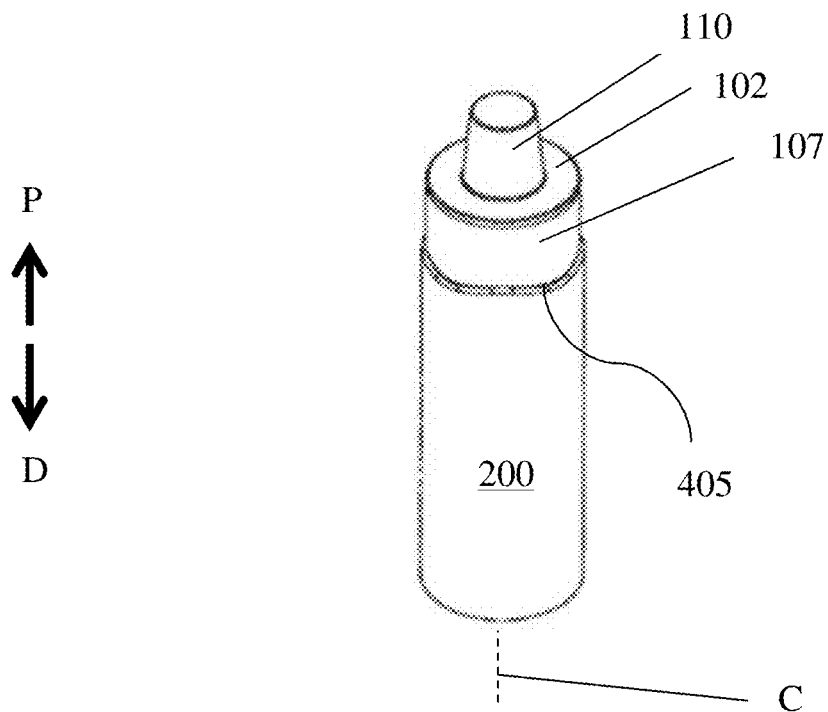
FIG. 4A shows a perspective view of the implant of FIGS. 1A-1C fully seated within the resected bone of FIG. 3.
Figure 4B:
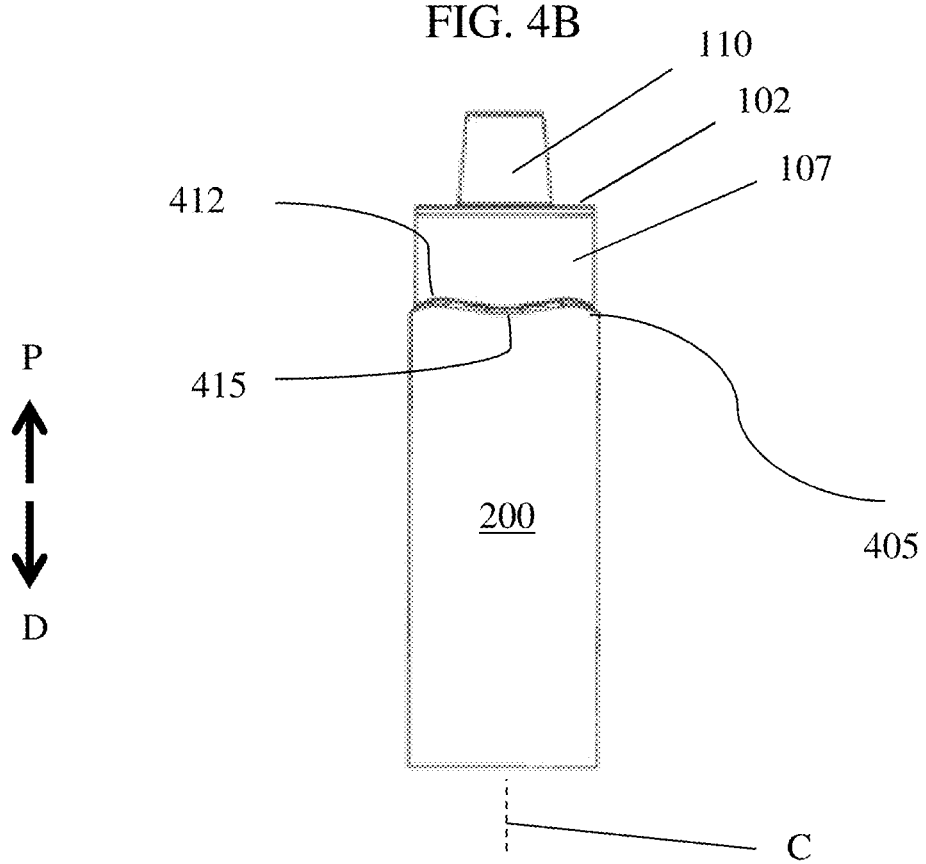
FIG. 4B shows a side view of the implant of FIG. 4A.

FIGS. 4A-4B show implant 100 positioned, fully seated within bone 200. During positioning, distal surface 105 may be engaged with outer surface 205 such that peaks 112 align with peaks 212 and valleys 115 align with valleys 215. Moreover, stem portion 120 may be inserted into a bore (not shown) in the outer surface 205 of bone 200. For example, the bore may be a medullary canal of bone 200. This may help improve implant fixation. In certain cases, distal end 125 of stem portion 120 may be curved or rounded to facilitate insertion.

When implant 100 is in position, peaks 112 and valleys 215 can help resist loosening of the implant because peaks 112 abut valleys 215 upon rotation of implant 100 with respect to bone 200. Similarly, valleys 115 also abut peaks 212 upon rotation of implant 100 with respect to bone 200.

When surfaces 105, 205 are engaged with each other, they may form bone-implant interface 405 shown in FIG. 5. As such, interface 405 has peaks 412 and valleys 415 that correspond to matching peaks 112, 212 and valleys 115, 215. Because the surfaces 105, 205 have matching wave patterns, interface 405 has no gaps between the engaging surfaces 105, 205. Good matching may help maximize surface contact between distal surface 105 of implant 100 and outer surface 205 of bone 200. In turn, this may help further improve implant fixation.

As shown in FIG. 5, peaks 412 and valleys 415 may each have an amplitude 414, 417 respectively. Here, amplitudes 414 and 417 are equal. In addition, FIG. 5 also shows a uniform wavelength 413 which may be defined as a distance between adjacent centers 416 of peaks 412.

Amplitude 414 of peak 412 may be defined as a distance between a center 416 of peak 412 and axis Pa. Here, all amplitudes 414 of peaks 412 are equal. Although amplitude 414 is discussed with respect to peaks 412, it may also be understood that peak 112 has an amplitude 114 (not shown) and peak 212 has an amplitude 214 (not shown). Thus, amplitudes 114 and 214 are also equal.

Similarly, amplitude 417 of valley 414 may be defined as a distance between a center 419 of valley 415 and axis Pa. Here, all amplitudes 417 of valleys 415 are equal. Although amplitude 417 is discussed with respect to valleys 415, it may also be understood that valley 115 has an amplitude 117 (not shown) and valley 215 has an amplitude 217 (not shown). Thus, amplitudes 117 and 217 are also equal.

FIGS. 1-5 show a wave pattern on distal surface 105 of implant 100 and a matching wave pattern on outer surface 205 of bone 200. In some applications, however, there may be different wave patterns on surfaces 105, 205. Depending on how the peaks/valleys 112, 115 align with peaks/valleys 212, 215, there may be gaps at the bone-implant interface. For example, there may be minimal surface contact area at the bone-implant interface. This may not be recommended due to poor matching between the distal and outer surfaces, which could lead to failure of implantation.

Also, in different embodiments, the distal surface may be straight and planar, while the outer surface includes a wave pattern. Alternatively, the distal surface may include a wave pattern, while the outer surface is straight and planar. Generally, if one engaging surface includes a wave pattern, while the other does not, there may be gaps at the bone-implant interface. Again, this may not be recommended due to poor matching between the distal and outer surfaces.

Figure 6A:
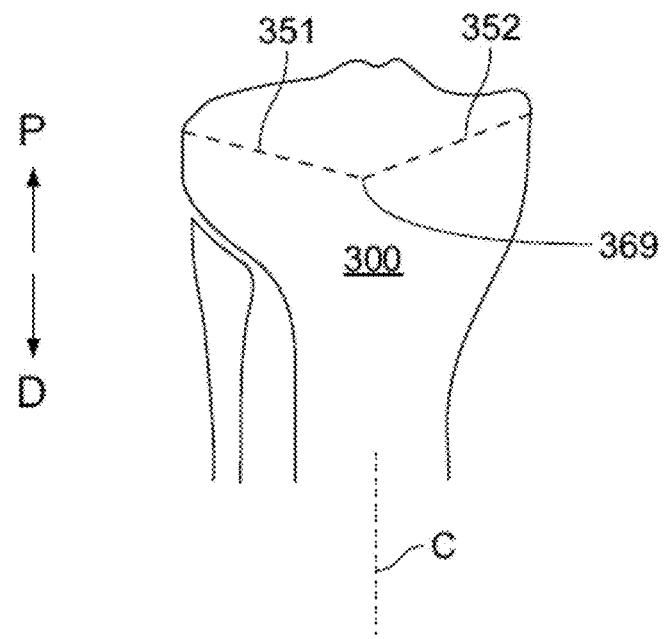
FIG. 6A shows a side view of another bone prior to a conical bone cut being made.

Additionally, instead of a straight planar bone cut (FIG. 2), a surgeon may choose to perform a conical bone cut (FIG. 6A) to expose an outer surface 305 of a bone 300. As shown in FIG. 6A, a surgeon may perform two angled bone cuts 351, 352 forming a cone with an apex 369 extending in the distal direction D. Thereafter, a surgeon may choose whether or not to further shape outer surface 305 of bone 300 using a robotic cutting tool to generate a wave pattern.

Figure 6B:
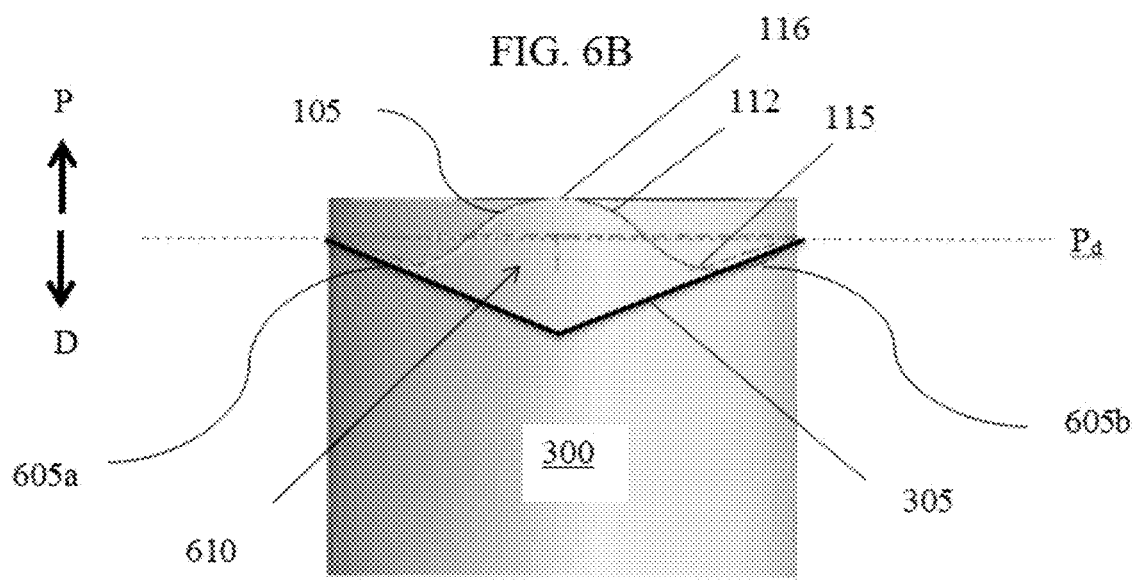
FIG. 6B shows a side view of the implant of FIGS. 1A-1C fully seated within the resected bone of FIG. 6A.

As shown in FIG. 6B, outer surface 305 of bone 300 does not include a wave pattern. Thus, there is a gap 610 between distal surface 105 and outer surface 305. As a result, there may be minimal surface contact area 605a, 605b at the bone-implant interface 605. In some cases, this can negatively affect implant fixation. In some other cases, a surgeon may actually desire to create gap 610 in order to later fill gap 610 with a bone graft or other bone substitute, such as allograft material such as allograft material polyetheretherketone, stainless steel or titanium. In turn, this may help promote bone ingrowth and improved implant fixation.

Moreover, in FIGS. 1-6, distal surface 105 is the only bone-engaging surface, but in different embodiments, proximal surface 102 may instead be the only bone-engaging surface, or both surfaces 102, 105 may be bone-engaging surfaces. Accordingly, it would be possible to include a wave pattern on distal surface 105, proximal surface 102, or both. It would also be possible to include the same or different wave patterns on surfaces 102, 105. In certain applications, it may also be possible to include a wave pattern on outer surface 107 wherein the peaks extend in a lateral direction away from the central longitudinal axis C and the valleys extend in a medial direction towards the central longitudinal axis C.

Furthermore, in different embodiments, implant 100 may or may not include a head portion 110 or a stem portion 120. Also, head portion 110 could be a female connector, instead of a male connector, to engage with other modular implant components. Alternatively, head portion 110 may include a different type of connector to engage with another piece of surgical equipment, such as a screw driver head.

In addition, surfaces 102, 105 may or may not be circular and surface 107 may not be cylindrical. Similarly, stem portion 120 may not be cylindrical. For example, in certain applications, a surgeon may desire the implant 100 to be an elliptical shape. It is also possible to vary a length of stem portion 120 among embodiments, wherein the length is defined as a distance between proximal and distal ends 122, 125. It is further possible to include protrusion features on stem portion 120 to better engage with the bore in the bone and provide for better fixation.

Further still, in some embodiments, proximal and distal surfaces 102, 105 may be angled with respect to one another. Distal surface 105 may also include a wave pattern spanning its entire surface rather than just circumferential perimeter 109. In addition, amplitudes 414, 417 and wavelength 413 may vary in different embodiments. For example, amplitudes may vary from peak to peak and from valley to valley. As another example, amplitude 414 may or may not be equal to amplitude 417. As yet another example, amplitudes 114, 117 may or may not be equal to amplitudes 214, 217. It is also possible for the wave pattern to have a non-uniform wavelength. In the same way, the desired wave pattern may not be periodic. In order to generate such differences in peaks and valleys, a surgeon may use burrs of different diameters when creating the wave pattern on the outer surface of the bone.

According to a second embodiment of the present disclosure, a surgeon or other designated user, such as a designer or technician, may wish to pre-operatively plan and design a unique wave pattern based on a particular bone deformity. In doing so, a surgeon may still maximize surface contact area at the bone-implant interface and also minimize long-term bone loss.

Figure 7:
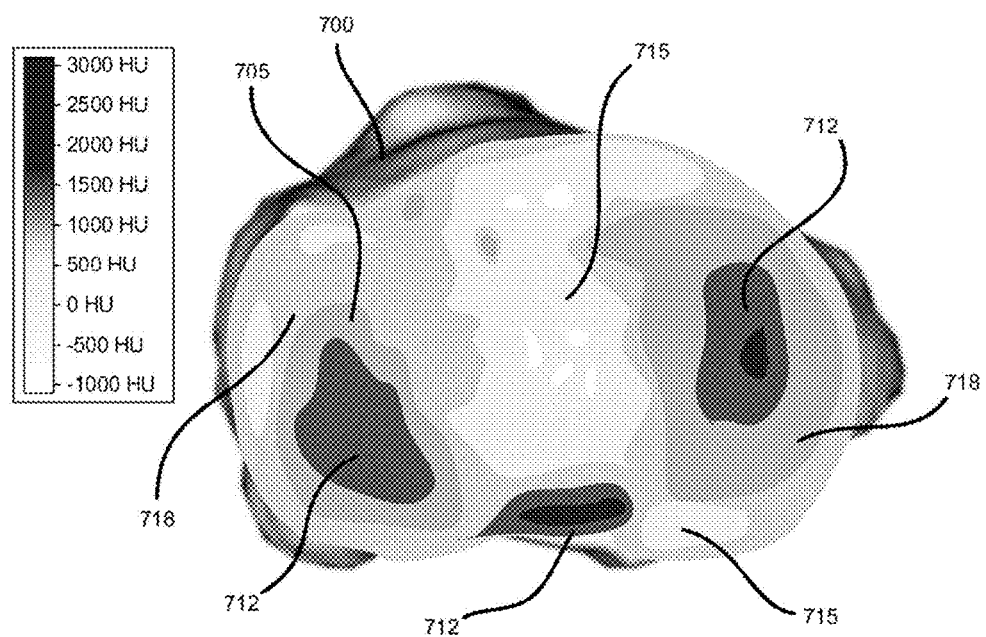
FIG. 7 shows one embodiment of a density visualization map of a bone.

First, a surgeon may choose to perform a straight planar bone cut, a conical bone cut, or some other bone cut to expose an outer surface 705 of bone 700. Then, the surgeon may use a software application to determine a bone density in Hounsfield units at various points across outer surface 705 and calculate an average bone density. As an example, FIG. 7 shows outer surface 705 of bone 700 at 8 mm bone cut depth.

Next, the surgeon may use the software application to assign a color on the RGB scale or gray scale to indicate areas of relatively high density 712 or relatively low density 715 in comparison to the average density. Preferably, relatively high density areas 712 have a bone density of at least 700 Hounsfield units. Then, the surgeon may use a 'Density Visualization Tool' as part of the software application to create a patient-specific color-map (FIG. 7) to visualize the relative densities of areas of bone 700. Here, relatively high density areas 712 are dark gray, while relatively low density areas 715 are light gray or white, and relatively moderate or average density areas 718 are a shade of gray falling between the dark and light gray. In other examples, if a RGB scale is utilized, the high density areas may be red, low density areas may be green, and moderate or average density areas may be yellow. Following, the surgeon may use the patient-specific color-map to design a unique wave pattern that may aim to preserve relatively high density areas 712 of bone 700 in order to reduce long-term bone loss.

The surgeon may then use the patient-specific color-map to determine the size, location and orientation of the implant with respect to the bone and whether a stem or keel portion is desired for additional fixation. Accordingly, the surgeon may also determine the size, location, and orientation of the stem if so desired. Thus, the surgeon is able to pre-operatively plan and design an implant that will provide good fixation.

Based on the patient-specific color-map, the surgeon may choose to include a unique wave pattern on either outer surface 705 of bone 700, a distal surface 805 of a bone implant 800, or both. With reference to a wave pattern on outer surface 705 having peaks extending in a proximal direction P and valleys extending in a distal direction D; any bone preserved to create peaks in outer surface 705 would preferably have a relatively high density and be better able to withstand high loading forces. Similarly, any bone resected to create valleys in outer surface 705 would preferably have a relatively low density. Accordingly, it is recommended to avoid resecting bone with relatively high density in order to minimize long-term bone loss.

Figure 8A:
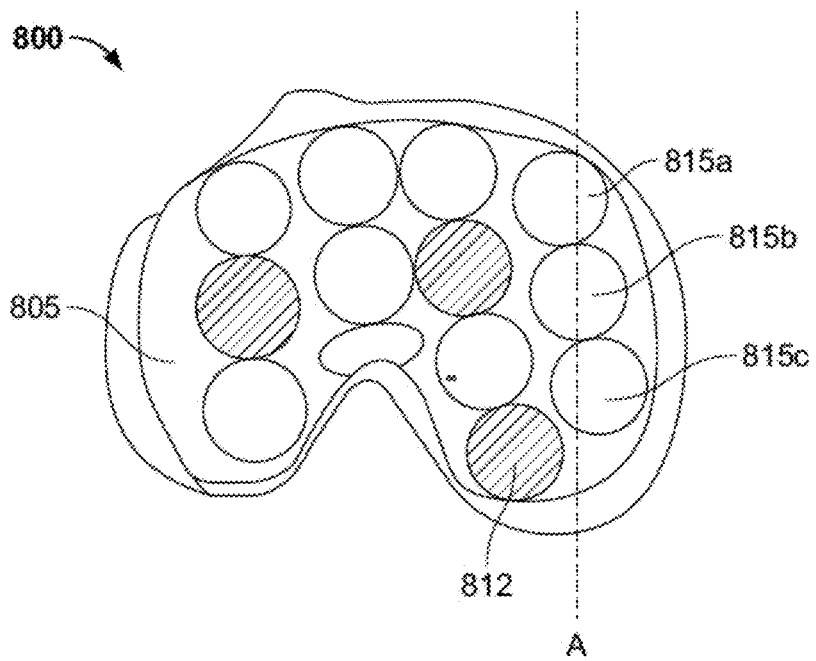
FIG. 8A shows a bottom view of a second embodiment of an implant of the present disclosure.

With reference to a wave pattern on distal surface 805 of implant 800; implant 800 has many similar features similarly numbered as implant 100 of FIGS. 1A-1C. That is, implant 800 has proximal surface 803 (not shown) and distal surfaces 805, wherein distal surface 805 runs along a distal axis Pa and includes a wave pattern (FIG. 8A). However, unlike implant 100 of FIGS. 1A-1C, implant 800 does not include a stem portion and the wave pattern spans across the entire distal surface 805.

As shown in FIG. 8A, the wave pattern on distal surface 805 includes peaks 812 and valleys 815, wherein the peaks 812 extend towards proximal surface 802 in a proximal direction P and valleys 815 extend away from proximal surface 802 in a distal direction D. Moreover, peaks 812 are designed to correspond to relatively high density areas 712 of bone 700 and valleys 815 are designed to correspond to relatively low density areas 715 of bone 700, when the implant 800 is in position, fully seated with respect to bone 700.

Figure 8B:
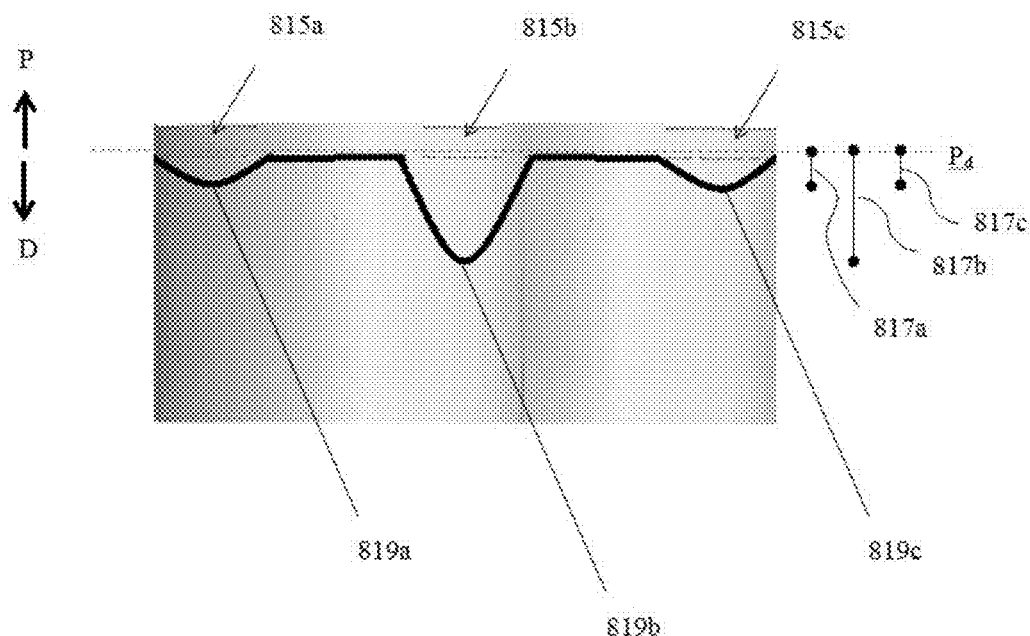
FIG. 8B shows a side view of the bone-implant interface of FIG. 8A.

Based on the patient-specific color-map, it is possible for valleys 815a-c to have different amplitudes 817a-c, wherein amplitude 817 is defined as a distance between a center 819a-c of valleys 815a-c and axis Pa. FIG. 8B shows a side view of valleys 815a-c taken along axis A (shown in FIG. 8A). Amplitude 817b is larger than amplitudes 817a and 817c. Accordingly, the largest amplitude 817b of valley 815b corresponds to the relatively lowest density bone area 715b. The same may be true for different peaks 812 wherein a largest amplitude 814 of peak 112 (not shown), defined as the distance between a center 116 of peak 112 (not shown) and axis Pa, corresponds to the relatively highest density bone area.

Alternatively, the surgeon may wish to use a standard color-map based on average bone densities of the 95$^{th}$ percentile of related population data for that particular bone. Thus, the surgeon may pre-operatively plan and design a standard implant with a standard wave pattern based on the standard color-map. Even if the surgeon will ultimately design a patient-specific implant with a unique wave pattern, it may be desirable to directly compare the standard color-map and patient-specific color-map. Then, the surgeon could better evaluate the risk of bone loss.

According to a third embodiment of the present disclosure, a surgeon may wish to pre-operatively plan and design a unique wave pattern for each of the proximal and distal surfaces of the implant. In doing so, a surgeon may still maximize surface contact area at the bone-implant interface and also provide for other means of fixation, such as inserting a fixation element through a fixation hole and into a bone.

Figure 9A:
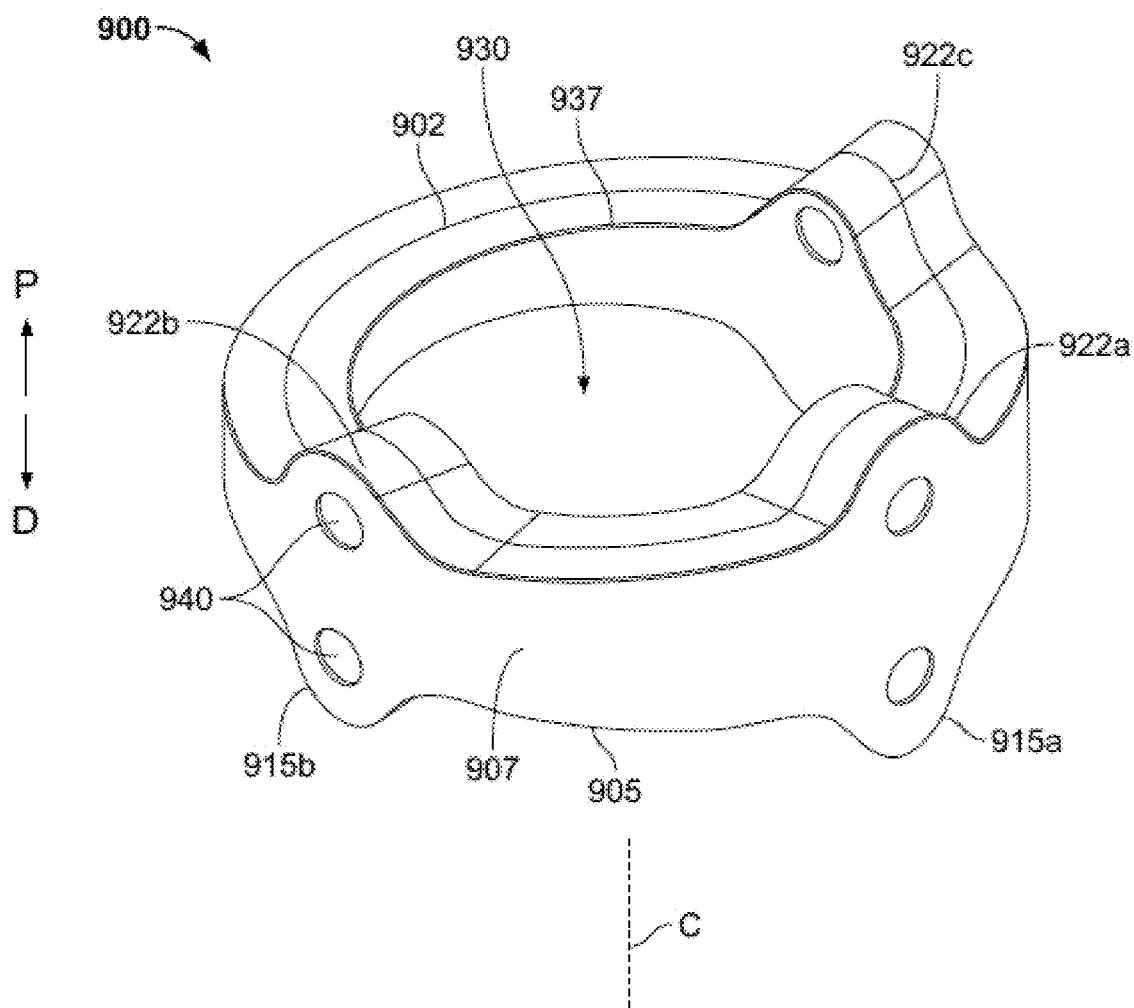
FIG. 9A shows a perspective view of a third embodiment of an implant of the present disclosure.
Figure 9B:
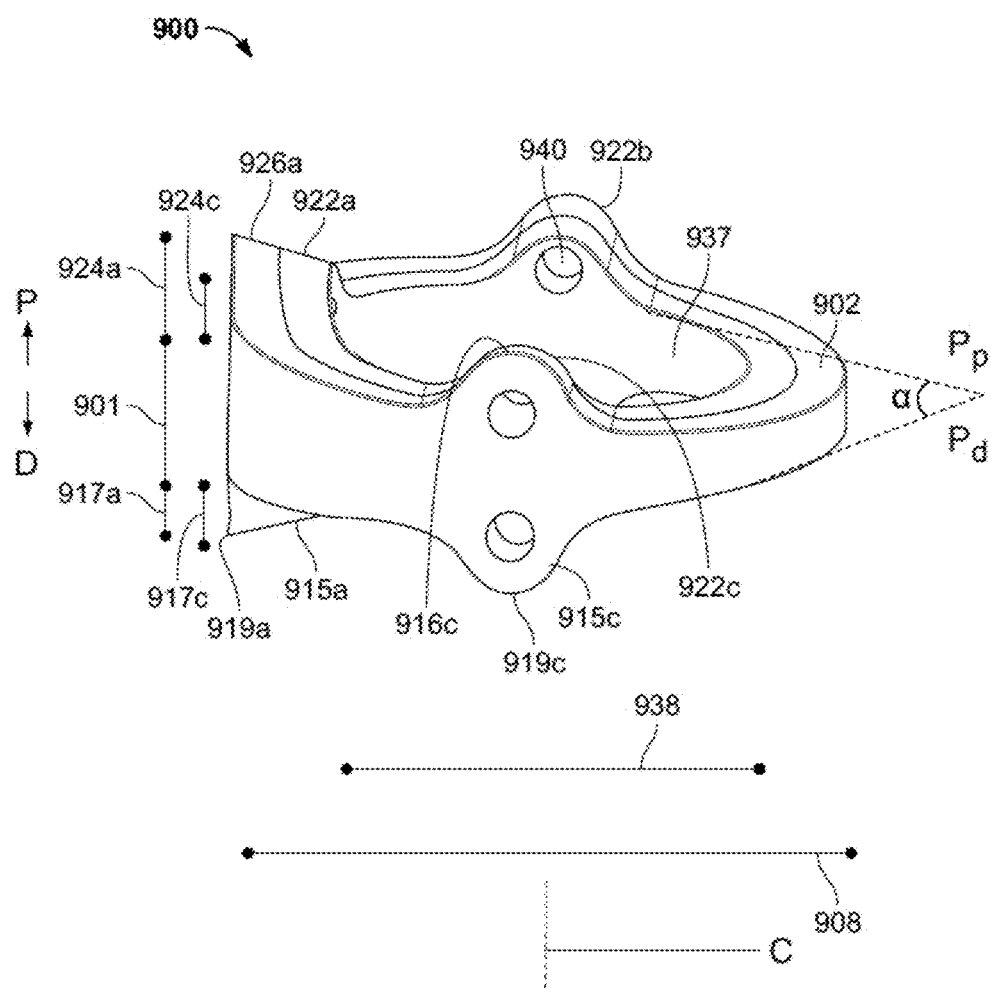
FIG. 9B shows a side view of the implant of FIG. 9A.

FIGS. 9A-9B show a bone implant 900 having a wave pattern on both proximal and distal surfaces 902, 905. Here, both proximal and distal surfaces 902, 905 are bone-engaging surfaces. For example, implant 900 may be disposed between proximal and distal bone fragments such that proximal surface 902 engages with an outer surface of a proximal bone fragment and distal surface 905 engages with an outer surface of a distal bone fragment.

Moreover, proximal and distal surfaces 902, 905 rung along axis Pp and axis Pd respectively. However, unlike bone implant 100 of FIGS. 1A-1C, axes Pp and Pa of implant 900 are angled away from one another. For example, angle α formed between axes Pp and Pa may be approximately 45 degrees. Additionally, implant 900 includes outer surface 907 extending between proximal and distal surfaces 902, 905.

As shown, proximal surface 902 includes peaks 922 extending away from distal surface 905 in a proximal direction P and does not include any valleys. Peak 922a has a larger amplitude 924a than an amplitude 924b of peak 922b, wherein amplitude is defined as the distance between a center 926 of a peak 922 and axis Pp. All peaks 922 are biased radially inwardly toward the central longitudinal axis C.

In contrast, distal surface 905 includes valleys 915 extending away from proximal surface 902 in a distal direction D and does not include any peaks. Valley 915a has a larger amplitude 917a than an amplitude 917b of valley 915b, wherein amplitude is defined as the distance between a center 919 of a valley 915 and axis Pa. All valleys 915 are also biased radially inwardly toward the central longitudinal axis C.

In the preferred embodiment, centers 926 of peaks 922 are aligned with centers 919 of valleys 915. This design may be desirable when a surgeon wants to minimize a profile 901 of implant 900, wherein the profile 901 is defined as a distance between proximal and distal surfaces 902, 905; and still provide good fixation.

In addition, proximal and distal surfaces 902, 905 of implant 900 may include an aperture 930 extending therethrough. Aperture 930 may be useful to allow for bone marrow to flow therein. Aperture 930 may also define an inner surface 937 having a diameter 938 that is smaller than a diameter 908 of outer surface 907. Additionally, inner and outer surfaces 937, 907 may include at least one fixation hole 940 extending therethrough, wherein the fixation hole 940 is adapted to receive a fixation element (not shown) at a plurality of angles with respect to the central longitudinal axis C.

Before implantation of implant 900, a surgeon may choose whether or not to further shape the outer surfaces of the proximal and distal bone fragments to also include a wave pattern, which may or may not be the same as the wave pattern on the respective bone-engaging surface. After implantation of implant 900, a surgeon may insert a fixation element through fixation hole 940 and into an adjacent bone for lateral-fixation or into an opposite bone for cross-fixation. Cross-fixation is possible because of the polyaxial fixation holes 940 and because peaks 922 and valleys 915 are biased radially inwardly toward the central longitudinal axis C.

In different embodiments, proximal and distal surfaces may be angled toward each other, rather than away from each other. The angle between axes Pp and Pa may also vary from 1 to 180 degrees depending on the severity of the deformity. The amount the peaks 922 and valleys 915 are biased radially inwardly can also vary between embodiments.

Furthermore, different embodiments of proximal surface 902 may include fewer or more than three peaks and/or may include at least one valley. Similarly, distal surface 905 may include fewer or more than three valleys and/or may include at least one peak. This all may depend on the desired number of fixation holes and whether or not the outer surface of the bone fragment includes a wave pattern. In some cases, a surgeon may also consider including fixation holes of different sizes, different orientations, and/or at staggered locations.

Overall, according to the present disclosure, a surgeon may design a wave pattern to be included on a bone-engaging surface of an implant, an implant-engaging surface of a bone, or both. In certain applications, an implant may include multiple bone-engaging surfaces with multiple wave patterns that could be the same or different. Ultimately, good matching between the engaging surfaces helps maximize surface contact area at the bone-implant interface.

As discussed, a wave pattern may include peaks and/or valleys which serve as rotational stabilization features for the implant with respect to the bone. That is, including a wave pattern on a bone-engaging surface helps prevent loosening or rotating of the implant with respect to the bone. Good stability also helps promote bone ingrowth which contributes to long term fixation of the implant. The peaks may have equal amplitudes or different amplitudes with respect to each other, and they may have equal amplitudes or different amplitudes with respect to the valleys. Moreover, the valleys may have equal amplitudes or different amplitudes with respect to each other.

In some applications, a surgeon may preoperatively plan a unique wave pattern that is designed to preserve high density bone. By using a software application to create a color map and visualize the relative densities of areas of the bone, a surgeon can make informed choices about the location of peaks or valleys in the wave pattern. Based on the color map, the surgeon may design the wave pattern such that peaks align with relatively high density bone areas and valleys align with relatively low density bone areas. Thus, preferably only low density bone may be resected to create valleys. For example, in certain cases, a surgeon may choose to include a wave pattern having only peaks or only valleys on the implant, on the bone, or both.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method of maximizing surface contact between an implant and an outer surface of a bone comprising:
    using a cutting tool to produce a wave pattern on the outer surface of the bone, the wave pattern having alternating curved peaks and curved valleys, each valley connecting adjacent peaks, each peak extending in a proximal direction and each valley extending in a distal direction; and
    positioning the implant such that a distal surface of the implant engages the outer surface of the bone.

2. The method of claim 1, wherein the positioning step includes disposing an adhesive on either the outer surface of the bone, the distal surface of the implant, or both.

3. The method of claim 1, further comprising producing a wave pattern on the distal surface of the implant.

4. The method of claim 3, wherein the wave pattern on the distal surface of the implant matches the wave pattern on the outer surface of the bone, and wherein the positioning step includes aligning the respective wave patterns.

5. The method of claim 3, further comprising producing a wave pattern on a proximal surface of the implant.

6. The method of claim 3, further comprising inserting a stem portion extending in the distal direction from the distal surface of the implant into a medullary canal of the bone, the stem having a smaller diameter than a diameter of the distal surface of the implant.

7. The method of claim 6, wherein the wave pattern spans only a circumferential perimeter of the distal surface of the implant.

8. The method of claim 1, further comprising engaging a head portion of a proximal surface of the implant with another modular implant component.

9. The method of claim 1, wherein the distal surface of the implant is porous such that the positioning step allows for bone in-growth.

10. The method of claim 1, further comprising planning the configuration of the wave pattern before the step of using the cutting tool.

11. A method of maximizing surface contact between an implant and an outer surface of a bone comprising:
producing a wave pattern on a distal surface of the implant, wherein the wave pattern includes alternating curved peaks and curved valleys, each valley connecting adjacent peaks, each peak extending in a proximal direction and each valley extending in a distal direction; and
positioning the implant such that the distal surface of the implant engages the outer surface of the bone.

12. The method of claim 11, further comprising determining relative densities of areas of the bone, wherein the wave pattern on the distal surface of the implant is preoperatively planned such that peaks align with relatively high density bone areas and valleys align with relatively low density bone areas.

13. The method of claim 11, wherein the positioning step includes disposing an adhesive on either the outer surface of the bone, the distal surface of the implant, or both.

14. The method of claim 11, further comprising producing a wave pattern on the outer surface of the bone, wherein the wave pattern on the distal surface of the implant matches the wave pattern on the outer surface of the bone, and wherein the positioning step includes aligning the respective wave patterns.

15. The method of claim 14, further comprising producing a wave pattern on a proximal surface of the implant.

16. The method of claim 11, further comprising inserting a stem portion extending in the distal direction from the distal surface of the implant into a medullary canal of the bone, the stem having a smaller diameter than a diameter of the distal surface of the implant.

17. The method of claim 16, wherein the wave pattern spans only a circumferential perimeter of the distal surface of the implant.

18. The method of claim 11, further comprising engaging a head portion of a proximal surface of the implant with another modular implant component.

19. The method of claim 11, wherein the distal surface is porous such that the positioning step allows for bone in-growth.

20. A method of maximizing surface contact between an implant and an outer surface of a bone comprising:
planning a configuration of a wave pattern on a distal surface of the implant and a configuration of a wave pattern on the outer surface of the bone, wherein each wave pattern includes alternating curved peaks and curved valleys, each valley connecting adjacent peaks;
producing the wave pattern on the distal surface of the implant after the planning step;
using a robotic cutting tool to produce the wave pattern on the outer surface of the bone after the planning step; and
positioning the implant such that the distal surface of the implant engages the outer surface of the bone and the respective wave patterns align.

* * * * *